(12) United States Patent
Corcoran-Henry et al.

(10) Patent No.: US 9,259,379 B2
(45) Date of Patent: Feb. 16, 2016

(54) ORAL CARE COMPOSITIONS FOR COMBATTING DENTAL EROSION

(71) Applicant: Glaxo Group Limited, Brentford (GB)

(72) Inventors: Ruth Corcoran-Henry, Brentford (GB); Soha Dattani, Harlow (GB); Christabel Fowler, Essex (GB); Geeta Patel, Harlow (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/929,852

(22) Filed: Jun. 28, 2013

(65) Prior Publication Data

US 2014/0037556 A1   Feb. 6, 2014

Related U.S. Application Data

(62) Division of application No. 13/132,371, filed as application No. PCT/EP2009/066473 on Dec. 7, 2009, now abandoned.

(30) Foreign Application Priority Data

Dec. 9, 2008  (GB) .................................. 0822434.7

(51) Int. Cl.
*A61Q 11/00* (2006.01)
*A61K 8/21* (2006.01)
*A61K 8/73* (2006.01)
*A61K 9/08* (2006.01)
*A61K 8/81* (2006.01)

(52) U.S. Cl.
CPC ... *A61K 8/21* (2013.01); *A61K 8/73* (2013.01); *A61K 8/731* (2013.01); *A61K 8/8182* (2013.01); *A61Q 11/00* (2013.01); *A61K 2800/594* (2013.01)

(58) Field of Classification Search
USPC ........ 424/49, 52, 57, 401, 484, 485; 433/215, 433/217.1; 514/901
See application file for complete search history.

(56) References Cited

U.S. PATENT DOCUMENTS

| 5,258,173 A | 11/1993 | Waterfield |
| 2003/0124065 A1 | 7/2003 | Majeti et al. |
| 2006/0008423 A1* | 1/2006 | Araya et al. .................... 424/49 |

FOREIGN PATENT DOCUMENTS

| WO | WO 00/13531 A2 | 3/2000 |
| WO | WO 2006/013081 A1 | 2/2006 |
| WO | WO 2006/100071 A1 | 9/2006 |
| WO | WO 2008/155345 A1 | 12/2008 |

OTHER PUBLICATIONS

Van Der Reijden W.A. et al.: "Influence of Polymers for Use in Saliva Substitutes on De- and Remineralization of Enamel in Vitro" Caries Research, S. Karger AG, Basel, CH, vol. 31, No. 3, Jun. 1, 1997 pp. 216-223, XP002128236; ISSN: 0008-6568 p. 216, p. 223.

Barbour Michele E. et al.: "An investigation of some food-approved polymers as agents to inhibit hydroxyapatite dissolution" European Journal of Oral Sciences, Munksgaard International Publishers, Copenhagen, DK LNKD-DOI:10.1111/J. 1600-0722.2005.00248. X, vol. 113, No. 6, Dec. 1, 2005 pp. 457-461, XP009132688; ISSN: 0909-8836 abstract.

* cited by examiner

*Primary Examiner* — Lezah Roberts
(74) *Attorney, Agent, or Firm* — Nora L. Stein; Theodore R. Furman (57) ABSTRACT

A oral care composition comprising a triple polymer system and a source of fluoride ions for combating (i.e. helping to prevent, inhibit and/or treat) dental erosion and/or tooth wear is described. Such compositions are also of use in combating dental caries.

3 Claims, 5 Drawing Sheets

ORAL CARE COMPOSITIONS FOR COMBATTING DENTAL EROSION

CROSS REFERENCE TO PRIOR APPLICATIONS

This application is a divisional of U.S. application Ser. No. 13/132,371, filed Jun. 2, 2011, which claims priority from GB Application No. GB 0822434.7, filed Dec. 9, 2008.

FIELD OF THE INVENTION

The present invention relates to an oral care composition comprising a triple polymer system and a source of fluoride ions for combating (i.e. helping to prevent, inhibit and/or treat) dental erosion and/or tooth wear. Such compositions are also of use in combating dental caries.

BACKGROUND OF THE INVENTION

Tooth mineral is composed predominantly of calcium hydroxyapatite, $Ca_{10}(PO_4)_6(OH)_2$, which may be partially substituted with anions such as carbonate or fluoride, and cations such as zinc or magnesium. Tooth mineral may also contain non-apatitic mineral phases such as octacalcium phosphate and calcium carbonate.

Tooth loss may occur as a result of dental caries, which is a multifactorial disease where bacterial acids such as lactic acid produce sub-surface demineralisation that does not fully remineralise, resulting in progressive tissue loss and eventually cavity formation. The presence of a plaque biofilm is a prerequisite for dental caries, and acidogenic bacteria such as *Streptococcus mutans*, may become pathogenic when levels of easily fermentable carbohydrate, such as sucrose, are elevated for extended periods of time.

Even in the absence of disease, loss of dental hard tissues can occur as a result of acid erosion and/or physical tooth wear; these processes are believed to act synergistically. Exposure of the dental hard tissues to acid causes demineralisation, resulting in surface softening and a decrease in mineral density. Under normal physiological conditions, demineralised tissues self-repair through the remineralising effects of saliva. Saliva is supersaturated with respect to calcium and phosphate, and in healthy individuals saliva secretion serves to wash out the acid challenge, and raises the pH so as to alter the equilibrium in favour of mineral deposition.

Dental erosion (i.e. acid erosion or acid wear) is a surface phenomenon that involves demineralisation, and ultimately complete dissolution of the tooth surface by acids that are not of bacterial origin. Most commonly the acid will be of dietary origin, such as citric acid from fruit or carbonated drinks, phosphoric acid from cola drinks and acetic acid such as from vinaigrette. Dental erosion may also be caused by repeated contact with hydrochloric acid (HCl) produced in the stomach, which may enter the oral cavity through an involuntary response such as gastroesophageal reflux, or through an induced response as may be encountered in sufferers of bulimia.

Tooth wear (ie physical tooth wear) is caused by attrition and/or abrasion. Attrition occurs when tooth surfaces rub against each other, a form of two-body wear. An often dramatic example is that observed in subjects with bruxism, a grinding habit where the applied forces are high, and is characterised by accelerated wear, particularly on the occlusal surfaces. Abrasion typically occurs as a result of three-body wear and the most common example is that associated with brushing with a toothpaste. In the case of fully mineralised enamel, levels of wear caused by commercially available toothpastes are minimal and of little or no clinical consequence. However, if enamel has been demineralised and softened by exposure to an erosive challenge, the enamel becomes more susceptible to tooth wear. Dentine is much softer than enamel and consequently is more susceptible to wear. Subjects with exposed dentine should avoid the use of highly abrasive toothpastes, such as those based on alumina. Again, softening of dentine by an erosive challenge will increase susceptibility of the tissue to wear.

Dentine is a vital tissue that in vivo is normally covered by enamel or cementum depending on the location i.e. crown versus root respectively. Dentine has a much higher organic content than enamel and its structure is characterised by the presence of fluid-filled tubules that run from the surface of the dentine-enamel or dentine-cementum junction to the odontoblast/pulp interface. It is widely accepted that the origins of dentine hypersensitivity relate to changes in fluid flow in exposed tubules, (the hydrodynamic theory), that result in stimulation of mechanoreceptors thought to be located close to the odontoblast/pulp interface. Not all exposed dentine is sensitive since it is generally covered with a smear layer; an occlusive mixture comprised predominantly of mineral and proteins derived from dentine itself, but also containing organic components from saliva. Over time, the lumen of the tubule may become progressively occluded with mineralised tissue. The formation of reparative dentine in response to trauma or chemical irritation of the pulp is also well documented. Nonetheless, an erosive challenge can remove the smear layer and tubule "plugs" causing outward dentinal fluid flow, making the dentine much more susceptible to external stimuli such as hot, cold and pressure. As previously indicated, an erosive challenge can also make the dentine surface much more susceptible to wear. In addition, dentine hypersensitivity worsens as the diameter of the exposed tubules increases, and since the tubule diameter increases as one proceeds in the direction of the odontoblast/pulp interface, progressive dentine wear can result in an increase in hypersensitivity, especially in cases where dentine wear is rapid.

Loss of the protective enamel layer through erosion and/or acid-mediated wear will expose the underlying dentine, and are therefore primary aetiological factors in the development of dentine hypersensitivity.

It has been claimed that an increased intake of dietary acids, and a move away from formalised meal times, has been accompanied by a rise in the incidence of dental erosion and tooth wear. In view of this, oral care compositions which help prevent dental erosion and tooth wear would be advantageous.

The present invention is based on the discovery that the presence of a triple polymer system consisting of xanthan gum, carboxymethyl cellulose and copovidone in an oral care composition comprising a source of fluoride ions enhances the efficacy of the fluoride ions in combating dental erosion.

Oral compositions comprising such a triple polymer system are described in WO 2006/013081, (Glaxo Group Ltd) for use in the treatment or alleviation of the symptoms of dry mouth by lubricating and hydrating the oral cavity. Such compositions may contain a source of fluoride ions as an anti-caries agent. There is no suggestion that such compositions can combat dental erosion or that the triple polymer system can enhance the efficacy of fluoride ions in combating dental erosion.

Van der Reijden et al (Caries Res., 1997, 31, 216-23) describes a range of in vitro experiments with saliva substitute compositions containing thickening agents to investigate their caries-protective properties, including the effect on demineralisation and remineralisation of enamel in vitro. The effect of a range of polymer materials on dissolution of hydroxyapatite crystals in 50, mM acetic acid at pH 5.0,, and a pH cycling experiment in which bovine enamel is exposed to demineralisation buffer (pH 4.8) and to remineralisation buffer (pH 7.0) containing a range of dissolved polymers, are described.

These experiments suggest that some polymers including xanthan gum and carboxymethylcellulose can reduce the demineralization of enamel in vitro and it is suggested that this may result from the formation of an adsorbed polymer layer on the enamel surface providing protection against acidic attacks.

WO 00/13531, (SmithKline Beecham) describes the use of various viscosity modifying polymer materials as tooth erosion inhibitors in acidic compositions for oral administration such as acidic beverages or acidic oral health care compositions. Examples of polymers include xanthan gum, carboxymethylcellulose and polyvinylpyrrolidone.

The role of certain polymer materials in protecting against dental erosion is described in WO 2004/054529, (Procter & Gamble) which claims a method of protecting against dental erosion comprising administering an oral care composition comprising a polymeric mineral surface active agent (ie a polyelectrolyte such as a polyphosphate, a polycarboxylate or certain carboxy-substituted polymers), wherein the polymeric mineral surface active agent is substantive to teeth and deposits a layer that protects teeth from erosive damage immediately after use and for at least one hour thereafter. It is suggested that such oral care compositions may optionally comprise a source of fluoride ions, although there is no teaching that the presence of a polymeric mineral surface active agent may enhance the efficacy of fluoride ions in protecting against dental erosion. It is also suggested that such oral compositions may comprise various thickening agents including xanthan gum and carboxymethyl cellulose. There is no suggestion that such thickening agents are substantive to teeth or can protect teeth against dental erosion.

Schaad et al (Colloids and Surfaces A: Physiochemical and Engineering Aspects 1994; 83; 285-292) describes the inhibition of dissolution of hydroxyapatite powder by adsorbed anionic polymers and suggests that some of these may be powerful agents for preventing the dissolution of enamel or bone tissues.

EP-A-691124, (Sara Lee) describes oral care products comprising a copolymer of N-vinylpyrrolidone and acrylic acid, said to result in enhanced enamel fluoride uptake in the tooth enamel. On page 11, the relative enamel fluoride uptake efficacy of various formulations containing different thickening agents is described, which thickening agents include carboxymethylcellulose, a combination of xanthan gum and a carbopol, a combination of xanthan gum and a copolymer of N-vinylpyrrolidone and acrylic acid and a combination of xanthan gum and a copolymer of a methylvinyl ether and maleic acid or anhydride.

French Patent No. 2755010, (Sara Lee) describes an oral care product containing fluoride comprising a combination of xanthan gum and a carboxylated vinyl polymer which combination is stated to enhance the efficacy of the fluoride in combating dental decay.

SUMMARY OF THE INVENTION

In a first aspect the present invention provides an oral care composition for combating dental erosion and/or tooth wear comprising a source of fluoride ions and a triple polymer system consisting of xanthan gum, carboxymethyl cellulose and copovidone.

The triple polymer system helps retain fluoride at the tooth surface thereby increasing the remineralisation of teeth and increasing the acid resistance of teeth, so providing a better surface protection against the effects of dental erosion than fluoride alone.

Accordingly, the compositions of the present invention are useful for enhancing the effectiveness of fluoride ions in combating dental erosion and/or tooth wear. Such compositions can both help protect and re-harden enamel from the effects of dietary acids.

Such compositions are also of use in combating dental caries.

DETAILED DESCRIPTION OF THE INVENTION

The xanthan gum may be present in an amount of 0.001, to 1.0% by weight of the total composition, for example from 0.005, to 0.5% or from 0.005, to 0.1% by weight of the total composition.

The carboxymethyl cellulose for use in the invention is in the form of the sodium salt i.e. sodium carboxymethyl cellulose. The carboxymethyl cellulose may be present in an amount of 0.02, to 20% by weight of the total composition, for example from 0.04, to 10% or from 0.1, to 1.0% by weight of the total composition.

The copovidone (which is a copolymer of vinylpyrrolidone and vinyl acetate, specifically a copolymer of 1-vinyl-2-pyrrolidone and vinyl acetate in a ratio of 3:2, by mass) may be present in an amount of 0.1, to 20% by weight of the total composition, for example from 0.2, to 10% or from 0.5, to 5% by weight of the total composition.

Examples of a source of fluoride ions for use in the present invention include an alkali metal fluoride such as sodium fluoride, an alkali metal monofluorophosphate such a sodium monofluorophosphate, stannous fluoride, or an amine fluoride in an amount to provide from 25, to 3500, pm of fluoride ions, preferably from 100, to 1500, ppm. A suitable fluoride source is an alkali metal fluoride such as sodium fluoride, for example the composition may contain 0.05, to 0.5% by weight of sodium fluoride, eg 0.1% by weight (equating to 450, ppm of fluoride ions), 0.205% by weight (equating to 927, ppm of fluoride ions), 0.2542% by weight (equating to 1150, ppm of fluoride ions) or 0.315% by weight (equating to 1426, ppm of fluoride ions).

Compositions of the present invention will contain appropriate formulating agents such as abrasives, surfactants, thickening agents, humectants, flavouring agents, buffering agents, sweetening agents, opacifying or colouring agents, preservatives and water, selected from those conventionally used in the oral care composition art for such purposes. Examples of these are described WO 2006/013081, (Glaxo Group Ltd) and WO 2004/054529, (Procter & Gamble), the contents of which are herein incorporated by reference.

Compositions of the present invention are typically formulated in the form of toothpastes, sprays, mouthwashes, gels, lozenges, chewing gums, tablets, pastilles, instant powders, oral strips and buccal patches. Preferred compositions are toothpastes and mouthwashes.

Additional oral care actives may be included in the compositions of the present invention.

Compositions of the present invention may further comprise a desensitising agent for combating dentine hypersensitivity. Examples of desensitising agents include a tubule blocking agent or a nerve desensitising agent and mixtures thereof, for example as described in WO 02/15809. Suitable desensitising agents include a strontium salt such as strontium chloride, strontium acetate or strontium nitrate or a potassium salt such as potassium citrate, potassium chloride, potassium bicarbonate, potassium gluconate and especially potassium nitrate.

A desensitising amount of a potassium salt is generally between 2, to 8% by weight of the total composition, for example 5% by weight of potassium nitrate can be used.

In a further aspect the present invention provides a mouthwash composition comprising a source of fluoride ions and a triple polymer system as hereinbefore defined for combating dental erosion and/or tooth wear.

The source of fluoride ions may be present in the mouthwash composition in an amount up to the maximum permitted by the regulations for any particular market. For example under EU regulations a mouthwash may contain up to 125, mg of ionic fluoride per single container of product. In the US a mouthwash for OTC use may contain no more than 225, ppm of fluoride. Generally the mouthwash composition comprises from 100, to 1500 ppm of fluoride ions, for example from 150, to 1000, ppm or from 200, to 600, ppm such as 225, ppm or 450, ppm of fluoride ions.

In such a mouthwash composition the source of fluoride ions may be an alkali metal fluoride, such as sodium fluoride.

Suitably the mouthwash composition comprises xanthan gum in an amount of 0.005, to 0.02% by weight of the total composition.

Suitably the mouthwash composition comprises carboxymethyl cellulose in an amount of 0.1, to 0.4% by weight of the total composition.

Suitably the mouthwash composition comprises copovidone in an amount of 0.5, to 1.5% by weight of the total composition.

Such mouthwash composition can be advantageously used together with a fluoride toothpaste, in particular with an enhanced efficacy fluoride toothpaste, for example of the type described in WO2006/100071,, which is incorporated herein by reference, and suitably comprises an alkali metal fluoride as the fluoride source, an amphoteric surfactant or a low ionic surfactant which is methyl sodium methyl cocoyl taurate or a mixture thereof as the surfactant, and a silica dental abrasive as the abrasive, the composition having a Relative Dentine Abrasivity (RDA) value from 20, to 60, and a pH in the range 6.5, to 7.5, and being free of an orthophosphate buffer, a water-soluble salt of a $C_{10-18}$, alkyl sulphate and a calcium salt Accordingly, in a further aspect, the present invention comprises an oral care regimen for combating dental erosion and/or tooth wear comprising using on a daily basis the mouthwash composition of the present invention and a fluoride toothpaste. Suitably the mouthwash and the fluoride toothpaste are each used at least twice daily in the oral care regimen of the present invention.

In order to improve consumer compliance the present invention also provides an oral care kit for combating dental erosion and/or tooth wear comprising a mouthwash composition of the present invention, a fluoride toothpaste, and instructions for their use in an oral care regimen of the present invention.

Compositions of the present invention may be prepared by admixing the ingredients in the appropriate relative amounts in any order that is convenient and if necessary adjusting the pH to give a desired value, for example from 4.0, to 9.5,, eg from 5.5, to 9.0,, such as from 6.0, to 8.0, or from 6.5, to 7.5.

The present invention also provides a method for combating dental erosion and/or tooth wear which comprises applying an effective amount of a composition as hereinbefore defined to an individual in need thereof.

The present invention also provides the use of a source of fluoride ions and a triple polymer system consisting of xanthan gum, carboxymethyl cellulose and copovidone in the manufacture of an oral care composition for combating dental erosion and/or tooth wear.

The invention is further illustrated by the following Examples.

EXAMPLE 1

Dynamic Secondary Ion Mass Spectrometry (DSIMS)

Dynamic Secondary Ion Mass Spectrometry is a semi-quantitative technique that allows rapid elemental depth profiling with nanometer scale depth resolution and parts per billion sensitivity, and chemical maps with sub-micron detail. DSIMS has previously been used to investigate the composition of enamel and to determine the degree of fluoride incorporation into human enamel surfaces. In this study, the effect of the presence of the triple polymer system on the incorporation of fluoride into human enamel surfaces containing artificial erosive lesions was investigated using DSIMS. In this experiment the triple polymer system consisted of 0.75% of copovidone, 0.2% of carboxymethyl cellulose and 0.01% of xanthan gum, all by weight of the total composition.

Acrylic resin-embedded human enamel specimens, ~2×2, mm in dimension, were polished flat using 1200, and 2400, grit silicon carbide paper. Specimens were then divided into one of four treatment groups (n=5): i) deionised water, ii) the triple polymer system in deionised water iii) 300, ppm fluoride solution (fluoride source=sodium fluoride) and iv) the triple polymer system in 300, ppm fluoride (fluoride source=sodium fluoride), each treatment solution having a pH falling within the range of about 6.5, to 7.0. Artificial erosive lesions were created in the enamel by immersing the specimens for 5, minutes in a 1.0% citric acid solution, pH 3.8. After subsequently washing the enamel with deionised water, specimens were placed under agitation in one of the solutions described above for 1 minute. A final washing step was performed (using deionised water) before DSIMS analysis was carried out. The extent of fluoride incorporated into the enamel/retained on the enamel was determined using DSIMS. Depth profiling mode was used initially to determine the relative fluoride concentration in the first few microns of the surface. This was followed by vertical sectioning of the samples, which were then embedding in epoxy resin and polishing. The resulting cross sections were gold coated and the fluoride distribution examined by DSIMS imaging over the enamel to a depth of ~200, µm. Data was acquired from multiple areas (of size 200, µm×160, µm and 100, µm×80, µm) of each specimen.

Figure 1:
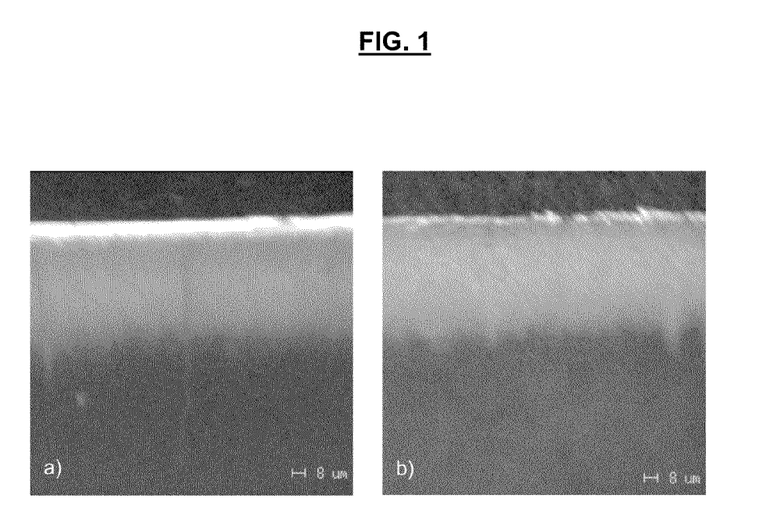
FIG. 1. shows the Dynamic Secondary Ion Mass Spectrometry cross sectional images of human enamel after exposure to solutions containing equal concentrations of sodium fluoride a) in the presence of the triple polymer system b) in the absence of the triple polymer system.

Representative cross sectional images from the enamel specimens are shown in FIG. 1. Specimens treated with either water only or the triple polymer system in water showed no evidence of fluoride within the specimens, at any depth (data not shown). Specimens treated with either the fluoride solution alone, or the fluoride solution containing the triple polymer system showed a fluoride containing band at the enamel surface, approximately 60, µm in depth in both cases (FIGS. 1a, and b). However, the enamel treated with the triple polymer system and fluoride contained substantially more fluoride in the top 6, µm of the surface of the tissue (FIGS. 1a, and b) than the enamel treated with fluoride alone.

EXAMPLE 2

White Light Interferometry (3DP)

The technique of White Light Interferometry provides rapid visualisation of surface topography, and determination of roughness parameters in non-contact mode where height resolution on the nanometer scale can be obtained. In this study, the effects of an artificial erosive challenge on human enamel were monitored using white light interferometry. The influence of pre-treatment of enamel with a solution containing the triple polymer system alone and in combination with fluoride was investigated. In this experiment the triple polymer system consisted of 0.75% of copovidone, 0.2% of carboxymethyl cellulose and 0.01% of xanthan gum, all by weight of the total composition.

Human enamel specimens were polished and divided into one of four treatment groups (n=5): i) deionised water, ii) 300, ppm fluoride (sodium fluoride) iii) triple polymer system in 300, ppm fluoride and iv) triple polymer system in deionised water, each treatment solution having a pH falling within the range of about 6.5, to 7.0. The specimens were incubated for 1, minute in the treatment solutions and subsequently washed with deionised water. Prior to acid exposure, specimen surfaces were partially masked by taping, in order to provide a reference point to enable any bulk tissue loss to be measured. During the erosion phase, specimens were immersed in 1.0% citric acid solution, pH 3.8, for 5 minutes. The surface topography of the specimens was investigated using an ADE PhaseShift MicroXAM White Light Interferometer. Data was acquired from multiple areas (of size 200, µm×160, µm and 100, µm×80, µm) of each specimen. After removal of the tape mask from the specimens, additional measurements were performed in order to determine whether any bulk tissue loss had occurred during the experiment.

Figure 2:
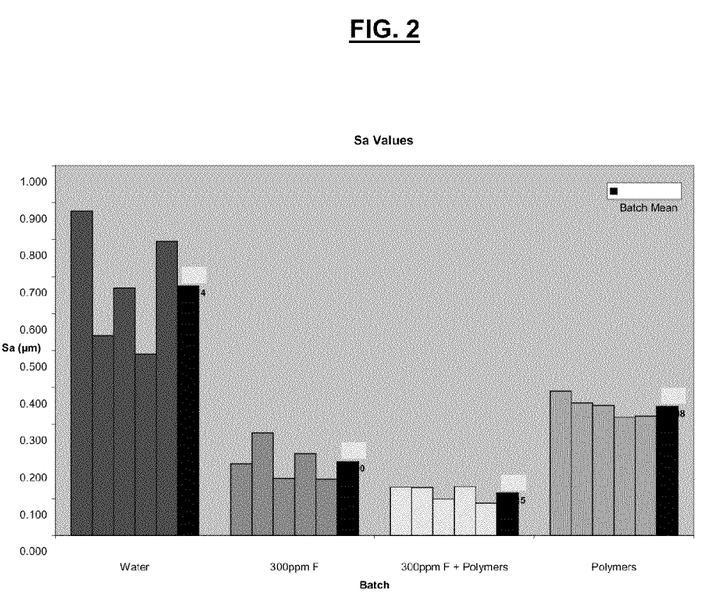
FIG. 2. shows the mean surface roughness values for enamel exposed to citric acid following treatment with various solutions.
Figure 3:
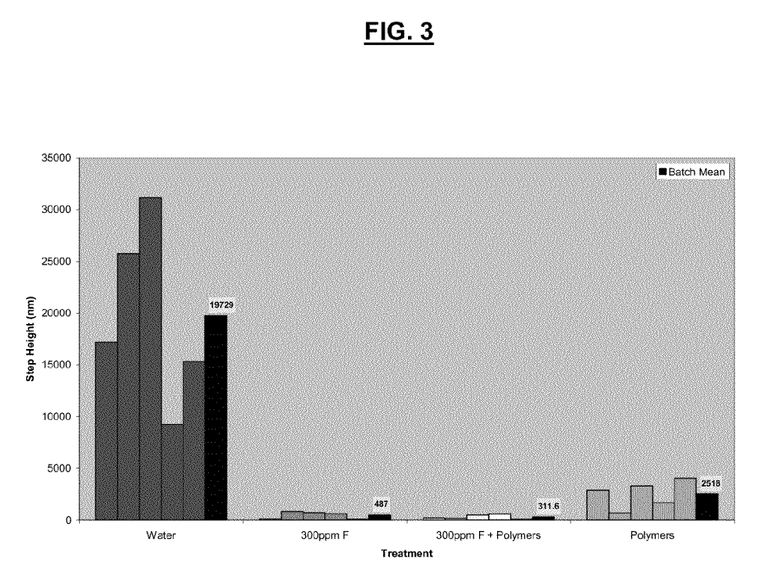
FIG. 3. shows the mean step height values for enamel exposed to citric acid following treatment with various solutions.

The results of the study are summarised in FIGS. 2 and 3. Measurement of Sa (surface roughness) and Sz (ten point height) for enamel treated with deionised water showed that the acidic challenge significantly increased the surface roughness of the specimens (FIG. 2). However, analysis of specimens that had been treated with solutions containing fluoride and/or the triple polymer systme showed that these pre-treatment solutions provided protection against the surface changes observed after water only pre-treatment. Enamel treated with the triple polymer system in combination with fluoride had the lowest Sa values, suggesting an additional protective effect of these two agents when employed in combination versus either agent alone (FIG. 2).

Profilometry measurements subsequently performed across the treated area/tape masked area interface showed that bulk tissue loss from specimens treated with the various solutions mirrored the trend in surface roughness values detailed above (FIG. 3). The greatest mean tissue loss was measured for specimens treated with deionised water only, and was approximately 20, µm. The mean tissue loss for specimens treated with the solution containing the triple polymer system alone was approximately 2.5, µm, and that for specimens treated with solutions containing fluoride alone or a combination of fluoride and the triple polymer system was less than 1, µm (FIG. 3).

EXAMPLE 3

Rehardening of Acid Softened Enamel

Artificial erosive lesions were prepared from polished human enamel mounted in acrylic resin. The lesions were prepared by contacting the mounted specimens for 30, minutes in a 1.0% w/w solution of citric acid, pH 3.8. The baseline hardness of each eroded specimen was determined using a Struers Duramin Microindentor, fitted with a Vickers diamond indenter. Hardness values were expressed as Vickers Hardness Numbers (VHN). A load of 1.961N was applied to the specimens, with a dwell time of 20, seconds. The specimens were then randomised and divided into 4, treatment groups (n=6).

Six enamel specimens were placed into one of two mouthrinse formulations, water or an agitated 1:3, w/w slurry prepared from an enhanced fluoride toothpaste (1450, ppmF), for 120s. The enhanced fluoride toothpaste is described in WO2006/100071, and is marketed as Sensodyne Pronamel. The two mouthrinse formulations were Colgate Plax Sensitive (225, ppmF) and ProRinse (450, ppmF), ie the test mouthwash of use in the present invention of the type described in WO 2006/013081,, and having a pH of 7.0, and comprising 0.1% of sodium fluoride and a triple polymer system consisting of 0.75% of copovidone, 0.2% of carboxymethyl cellulose and 0.01% of xanthan gum, all by weight of the total composition. The Sensodyne Pronamel toothpaste treatment leg was included in the study to act as a benchmark in order to provide validation for the study. The specimens were then removed and placed in mucin-free artificial saliva. Specimen rehardening was determined using microindentation after 24, hrs and 48, hrs. Six indents were obtained for each specimen at each time point.

Figure 4:
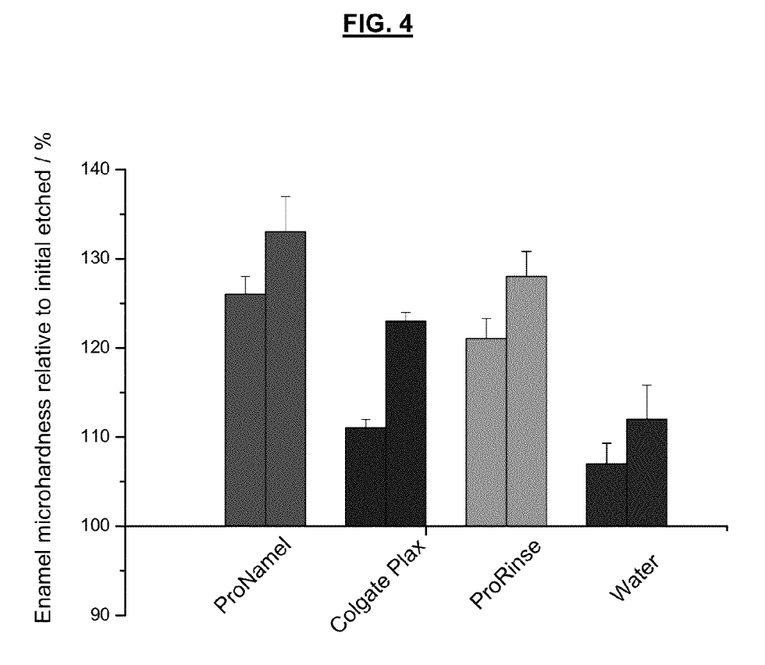
FIG. 4. shows the rehardening of human enamel artificial erosive lesions over 48, hrs after treatment with mouthrinse formulations (or Sensodyne Pronamel toothpaste).

The results of the rehardening study are summarised in FIG. 4. The values for enamel hardness have been normalised relative to those obtained after acid softening of the enamel. Thus the data at subsequent time points reflects rehardening of the enamel. All the enamel specimens rehardened during the period in which they are exposed to artificial saliva, and treatment with either mouthrinse formulation or Sensodyne Pronamel toothpaste resulted in statistically greater rehardening than treatment with water at both timepoints. In addition, after 24, hrs remineralisation, treatment with either Sensodyne Pronamel toothpaste or ProRinse lead to statistically greater rehardening compared to the Colgate Plax Sensitive mouthrinse. However, after 48, hrs incubation in the artificial saliva, there was no difference between the extent of remineralisation following treatment with either of the two mouthrinse formulations or the dentifrice.

EXAMPLE 4

Protection Against Effects of Acid Erosion

The study performed involved exposure of human enamel to 1% citric acid (pH 3.8), following a 2, minute treatment with one of the two mouthrinse formulations listed above (employed in the rehardening study), water or Sensodyne Pronamel toothpaste. Specimens were washed with water in between treatments and acid exposure. Acid erosion times investigated were 10, 20, and 30, minutes, and microhardness measurements were made at each time point, after washing the specimens thoroughly with distilled water again. Six indents were obtained for each enamel specimen at all time points. Each treatment was performed on six individual specimens.

Figure 5:
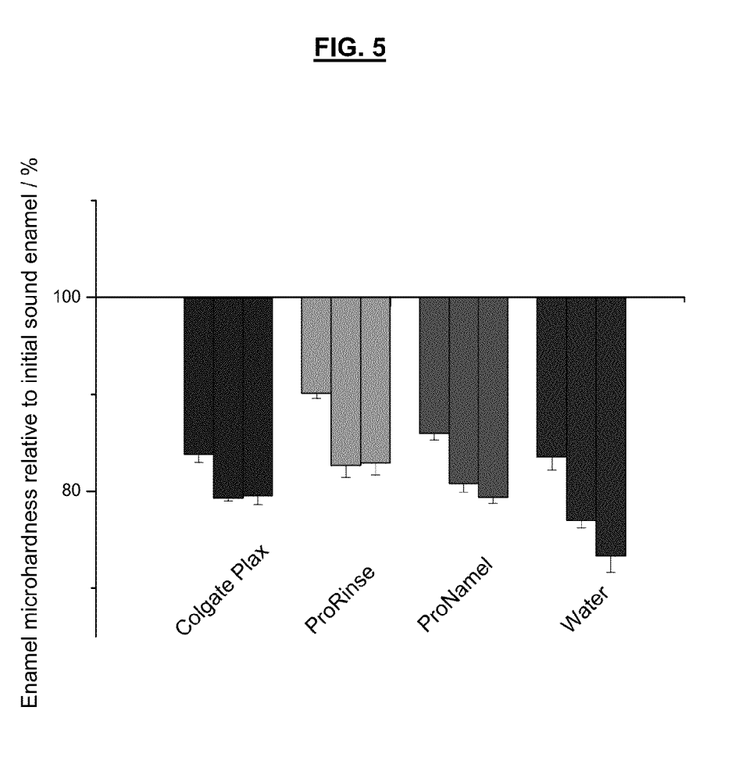
FIG. 5. shows the relative microhardness values for human enamel exposed to citric acid following treatment with mouthrinse formulations (or Sensodyne Pronamel Toothpaste).

The results of the softening study are summarised in FIG. 5. The values for enamel hardness have been normalised relative to the individual baseline microhardness values, thus data at subsequent time points reflects softening of the enamel. After 10, minutes acid exposure, the prorinse formulation provided statistically greater protection against enamel surface softening than any of the other treatments. After 20, minutes acid exposure, the Prorinse mouthrinse and Sensodyne Pronamel toothpaste treatments lead to statistically less softening of the enamel than the water treatment, but directionally less softening than the Colgate Plax Sensitive mouthrinse treatment. At the 30, minute erosion timepoint, the Prorinse mouthrinse formulation provided statistically greater protection against surface softening than the water treatment, and directionally greater protection against softening than the Colgate Plax Sensitive mouthrinse.

The invention claimed is:

1. A method of providing enhanced protection of teeth against dental erosion and/or toothwear comprising applying to teeth whose enamel has been softened by dietary acid an oral care composition comprising 0.05%-0.5% by weight sodium fluoride, 5% by weight potassium nitrate, and a triple polymer system consisting of 0.005% to 0.02% by weight xanthan gum, 0.1, to 0.4% carboxymethylcellulose and 0.5% to 1% by weight copovidone.

2. The method according to claim 1 wherein the composition is in the form of a mouthwash.

3. The method according to claim 1 wherein the pH of the composition is in the range 6.5, to 7.5.

* * * * *